US005855557A

United States Patent [19]
Lazenby

[11] Patent Number: 5,855,557
[45] Date of Patent: Jan. 5, 1999

[54] ULTRASONIC IMAGING SYSTEM AND METHOD FOR GENERATING AND DISPLAYING VELOCITY FIELD INFORMATION

[75] Inventor: John C. Lazenby, Fall City, Wash.

[73] Assignee: Siemens Medical Systems, Inc., Iselin, N.J.

[21] Appl. No.: 775,234

[22] Filed: Dec. 30, 1996

[51] Int. Cl.⁶ ....................................................... A61B 8/00
[52] U.S. Cl. ............................................. 600/443; 600/453
[58] Field of Search ........................ 128/660.02, 662.06, 128/660.07–661.1; 600/443, 442, 438, 453–457

[56] References Cited

U.S. PATENT DOCUMENTS

| | | | |
|---|---|---|---|
| 4,830,015 | 5/1989 | Okazaki | 128/660.04 X |
| 4,932,415 | 6/1990 | Angelson et al. | 128/661.09 |
| 5,088,498 | 2/1992 | Beach et al. | 128/661.07 |
| 5,099,848 | 3/1992 | Parker et al. | 128/661.07 |
| 5,105,816 | 4/1992 | Shimura et al. | 128/661.08 |
| 5,183,046 | 2/1993 | Beach et al. | . |
| 5,285,788 | 2/1994 | Arenson et al. | 600/443 X |
| 5,622,174 | 4/1997 | Yamazohi | 128/661.09 |

OTHER PUBLICATIONS

Parker, et al.: "A Review of Imaging Techniques for Assessing the Elastic Properties of Tissue," Dept. of Electrical Engineering, Univ. of Rochester, Rochester, NY 14627, 4 Jun. 1996, pp. 1–20.

*Primary Examiner*—Francis J. Jaworski
*Attorney, Agent, or Firm*—Jeffrey Slusher

[57] ABSTRACT

A system interrogates a region with ultrasound and then generates a vector field of values representing the velocity sensed at a plurality of image element positions. Spatial changes in the velocity vector field are then determined and displayed to the user, preferably in real time. The spatial changes include divergence and/or the rotation (also known as "curl") of the velocity vector field. In order to enable display of the vector spatial change information, either magnitude values, projected values, or color-coded vector information may be computed and displayed. In order to reduce the effect of noise on differentiation operations, the system preferably smooths the velocity vector field before, after or at the same time as it determines divergence or rotation.

12 Claims, 2 Drawing Sheets

ULTRASONIC IMAGING SYSTEM AND METHOD FOR GENERATING AND DISPLAYING VELOCITY FIELD INFORMATION

BACKGROUND OF THE INVENTION

1. Field of the Invention

This invention involves a system and a method for generating and displaying velocity field information, especially in the context of diagnostic ultrasonic imaging.

2. Description of the Related Art

For centuries, if not millennia, physicians have pinched, prodded, pulled, and poked their often cringing patients in order to better diagnose internal illnesses. In other words, physicians have long used palpation to find abnormalities in tissue. The reason for this is that the elasticity of tissue, that is, the way in which it expands or contracts in response to an externally or internally applied pressure, gives useful diagnostic information about the tissue. For example, when blood is pumped into tissue by the heart, the tissue contracts and expands in time with the cardiac cycle. In general, the more an area then expands, the more blood it may be receiving, or the more elastic it may be.

A plethysmograph is a device used by physicians to measure the expansion and contraction of tissue caused by blood flowing through the tissue. It is used by placing a fluid-filled cuff around a limb and then measuring the displacement or pressure change of the fluid. A significant drawback of this device, however, is that it gives information only about the general properties of a limb but no specific information about individual structures (for example, an artery or a muscular lesion) within the limb, or the relationship between an internal structure and surrounding structures. Moreover, devices such as the plethysmograph are unsuitable for use in examining the elasticity of organs such as the heart—squeezing a patient's chest hard enough to feel changes in his heart tissue or liver would probably render the whole diagnostic procedure moot.

It has been proposed that one could use ultrasonic imaging techniques in order to assess the elastic properties of tissue. For example, the following U.S. patents describe a technique for ultrasonic plethysmography:

U.S. Pat. No. 5,088,498 (Beach et al., 2 Feb. 1993); and

U.S. Pat. No. 5,183,046 (Beach et al., 18 Feb. 1992).

Furthermore, the article "A review of imaging techniques for assessing the elastic properties of tissue," Parker, Gao, Lerner, and Levinson, Dept. of Electrical Engineering, Univ. of Rochester, Rochester, N.Y. 14627, discusses various techniques for assessing tissue elasticity. These known methods are either difficult to implement in a normal clinical setting, do not allow for imaging in real time, or fail on both counts.

What is needed is a way to assess the elastic properties of tissue (including other properties relating to the local expansion and contraction of the tissue) with an easy-to-use system that is able to provided the information in real time.

SUMMARY OF THE INVENTION

The invention provides a system that interrogates a region with ultrasound and then generates a vector field of values representing the velocity sensed at a plurality of image element positions. Spatial changes in the velocity vector field are then determined and displayed to the user, preferably in real time. The spatial changes include divergence and/or the rotation (also known as "curl") of the velocity vector field. In order to enable display of the vector spatial change information, either magnitude values, projected values, or color-coded vector information may be computed and displayed. Determination of the divergence or curl is preferably preceded by or combined with smoothing of the velocity vector field in order to reduce the effect of noise on differentiation operations.

DETAILED DESCRIPTION

Figure 1:
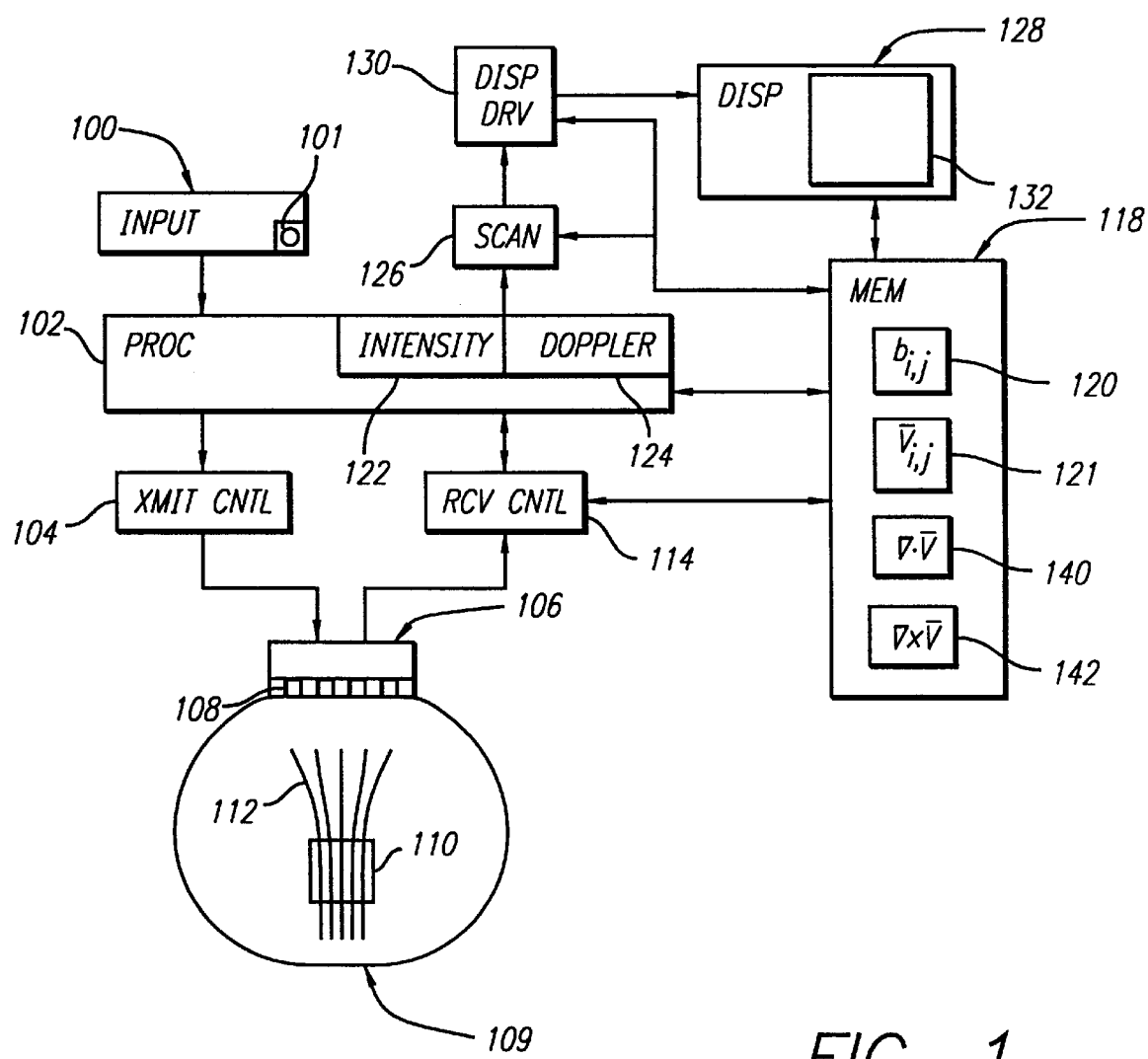
FIG. 1 is a block diagram of a preferred embodiment of a system according to the invention for generating an image representing a scanned region as a velocity vector field, and for generating and displaying changes over the velocity field according to the invention.

FIG. 1 illustrates the main components of an ultrasonic imaging system according to the invention. The user enters various conventional scan parameters into an input unit 100, which typically includes such devices as a keyboard 101, knobs, and buttons. The input unit is connected to a processing system 102, which will typically be an electrically connected and cooperating group of processors such as microprocessors and digital signal processors; the processing system may, however, also be implemented by a single processor as long as it is fast enough to handle the various tasks described below.

As in known systems, the processing system 102 sets, adjusts, and monitors the operating parameters of a conventional transmission control circuit 104. This control circuit 104 generates and applies electrical control and driving signals to an ultrasonic probe 106, which includes an array piezoelectric elements 108. As is well known in the art, the piezoelectric elements generate ultrasonic waves when electrical signals of the proper frequency are applied to them.

By placing the probe 106 against the body 109 of a patient, these ultrasonic waves enter a portion 110 (an interrogation region) of the patient's body. By varying the phasing, amplitude, and timing of the driving signals in a conventional manner, the ultrasonic waves are focussed to form a scan beam comprising a series of scan lines 112 that typically fan out from the probe.

In the most common applications of ultrasonic scanning, with linear arrays, the interrogation region 110 is scanned as a pattern of 2-D planes in order to generate 2-D image information, such as a spatial map of the intensity of echo signals returned from the interrogation region, or a 2-D map of the velocity of some tissue movement within the region. Other techniques using both one- and two-dimensional ultrasound arrays are, however, known that allow scan beams to lie in different planes and thus to generate 3-D representations of the scanned region, and to sense flow with three independent velocity components. The invention is able to operate with both 2-D and 3-D interrogation regions. The manner in which ultrasonic scanning signals are controlled, generated, and applied to a patient's body is well understood in the art and is therefore not described further.

Ultrasonic echoes from the waves transmitted into the body return to the array 108 in the probe 106. As is well understood, the piezoelectric elements in the array convert the small mechanical vibrations caused by the echoes into corresponding radio-frequency (RF) electrical signals. Amplification and other conventional signal conditioning is then applied to the return signals by a reception controller 114. This processing includes, as needed, such known signal conditioning as time-gating, gain compensation, and diffraction compensation, in order to identify the echo signals that correspond to each scan plane of the interrogation volume 110. The type of conventional signal processing needed will in general depend on the particular implementation of the invention and can be chosen using known design methods.

The reception controller 114, all or part of which is normally integrated into the processing system 102 itself, converts the ultrasonic, radio-frequency (RF) return signals (typically on the order of a few to tens of megahertz) into lower frequency ranges for processing, and may also include analog-to-digital conversion circuitry. This is well known in the art of ultrasonic imaging.

In systems that generate a representation of the interrogation region as a discretized pattern of brightness or signal intensity values $b_{i,j}$, ($b_{i,j,k}$ for 3-D imaging) the down-converted power values for the two-dimensional interrogation region are stored in a memory 118 as image frame data 120, after conventional beamforming. An intensity-determining portion 122 of the processing system 102 may be included to perform the conventional calculations necessary for relating returned echo signal strengths to a predetermined range of intensity values.

The Doppler shifts and/or the power Doppler spectra for the various echo signals are also determined, with necessary conventional calculations being performed in a Doppler/velocity-determining portion 124 of the processing system 102. Using the Doppler data and any known technique, the Doppler/velocity-determining portion 124 calculates a velocity vector $\bar{v}_{i,j}$ for each position (i,j) (for the 2-D case) or $\bar{v}_{i,j,k}$ for each position (i,j,k) (for the 3-D case) in the discretized pattern representing the scanned interrogation region.

Each frame of the image is represented and stored digitally as an array of acoustic power or intensity values $b_{i,j}$ and velocity vectors $\bar{v}_{i,j}$ (or $\bar{v}_{i,j,k}$ for 3-D imaging) for the image elements that make up the frame. These values $b_{i,j}$ and $\bar{v}_{i,j}$ are stored in respective memory portions 120, 121. Each set of frame data corresponds to one image frame, that is, to a 2-D cross section or 3-D sub-volume of the interrogation volume. (Three-dimensional data arrays may also be used in systems that do not need to build up 3-D images from 2-D frames, but rather that directly compile 3-D image data. In such case, $b=b_{i,j,k}$ and $\bar{v}=\bar{v}_{i,j,k}$)

Note that the invention provides a new method of processing and displaying information about the field of velocity values and will in general not need the brightness values at all. These are included in the description of the invention, however, first, by way of comparison with known systems, and, second, since display modes involving image brightness values are found in most existing ultrasound imaging systems anyway. Moreover, it is possible in certain applications of the invention to superimpose color-coded velocity field data onto, or to display it along side of, conventionally generated intensity-based images. Such dual-mode imaging would in many cases aid the user in locating structural boundaries and in interpreting the displayed information.

The interrogation region is normally not in the same shape as what the user wants to see displayed, and even when it is, the digital acoustic intensity values that make up the frame data are normally not in a form suitable for driving a conventional gray-tone or color display directly. The acoustic intensity or velocity values for an image frame are therefore applied to a conventional scan converter 126, which converts the digital acoustic values into display intensity values that are suitable for use in driving a display device 128.

Note that even vector-valued data such as velocity will normally need to be converted into a form suitable for display. This can be done in any conventional manner, such as reducing the velocity values to their magnitudes (speed) and displaying speeds using different display intensities. One may also color-code directional information into the display so that, for example, the faster tissue moves in one direction the brighter red it is displayed, whereas the faster it moves in the opposite direction the brighter blue it is displayed. As is explained below, the invention provides for generating both scalar and vector-valued data as functions of the vector-valued velocity data that the system generates.

The display device 128 typically includes or is connected to a conventional display driver 130 and includes a screen 132 (for example, LED or CRT) that is divided into an X-Y (or polar) matrix or pattern of picture elements or "pixels" that make up an image that the user can view and interpret. Note that a displayed image element will often be made up of more than one pixel, but that this will depend on the relative resolutions of the scan and of the display. The invention does not require any particular relative resolution.

Assume that one uses known techniques to measure the velocity of some tissue movement within the interrogation region. This movement is commonly the flow of blood within a vessel or an organ, but it may also be the movement of tissue such as the walls of the vessel or organ, the movement of a muscle, the changes in compressed layers of tissue, and so on. If all one is interested in is velocity information in one direction, then it is sufficient to focus a single beam on a given sample volume and to sense and measure the Doppler shift of the return signals from the beam. In order to get information sufficient to identify motion velocity components within the sample volume in two dimensions (two non-parallel velocity components) then one must normally focus at least two beams on the sample volume from different angles (for example, by using interleaved element arrays). In order to determine velocity components in all three directions in space, a 3-D beam must be generated in an analogous manner.

In the most generalized embodiment of the invention, velocity components in all three orthogonal directions will be generated and stored for each data point in an image frame. In order to save storage space or increase processing speed at the expense of resolution and, possibly accuracy, it is also possible to store single velocity vectors for each of predetermined groupings of data points, as long as one can assume that velocity is relatively constant over the region of a chosen group. Most existing systems, however, store image data for 2-D frames, and velocity components only in the plane of the frame are calculated and stored. The invention may be used to advantage in either case.

Figure 2:
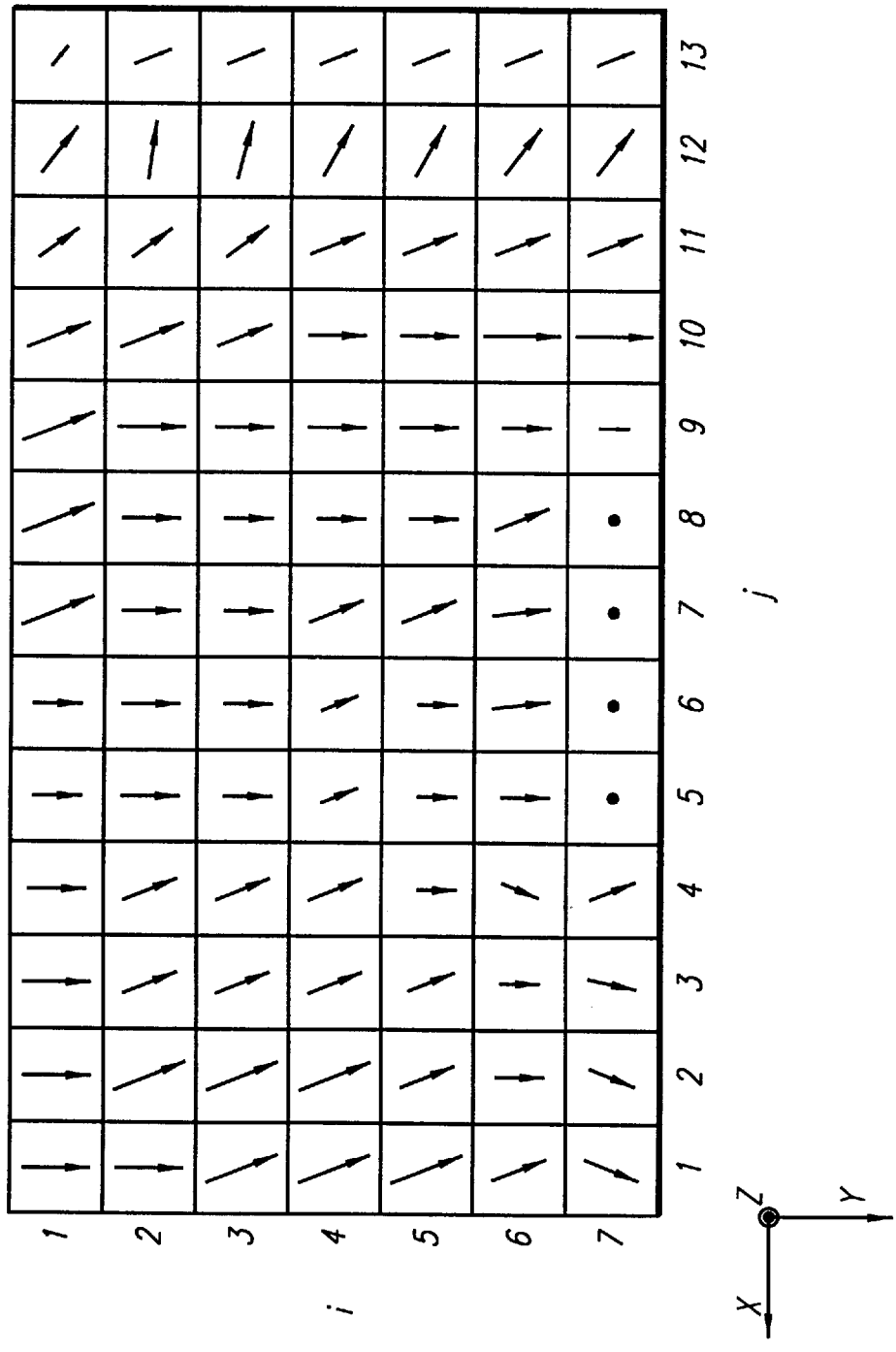
FIG. 2 illustrates a velocity vector field.

FIG. 2 illustrates graphically a 7×13 portion of a discrete velocity vector field $\bar{v}=\bar{v}_{i,j}$ that would be stored numerically in the memory portion 121. An x-y-z coordinate axis is also shown for reference, with the z-axis pointing up out of the plane of the figure. In applications in which 3-D velocity data is computed and stored, each value in the velocity vector field will have three components, including a z-axis component.

For purposes of illustration, assume that each "box" of the figure represents an image element. Assume further that the length of the arrow in each box corresponds to its magnitude (speed) and the direction in which the arrow points is the sensed direction of tissue movement for the corresponding portion of the interrogation region. Dots (for example, at positions (i,j)=(7,5), (7,6), (7,7), (7,8)) represent regions where no motion is sensed.

In the illustrated example, the movement of tissue is generally downward, in the positive y-direction, with a relatively small rightward movement, that is, in the negative x-direction, for elements in columns j=1, . . . , 10. The movement is faster along the top and left edges than near the center and bottom left. Consider the region represented by the elements at positions (4,5), (4,6), (5,5) and (5,6). In this region there is much less movement than in the elements surrounding it. This implies that the surrounding tissue above and, to some extent, to the left, of this region is undergoing some compression. This is even easier to see at positions (6,6), . . . , (6,9)—there, there is a clear downward motion that comes to a stop in the underlying tissue regions at position (7,5), . . . , (7,8).

As FIG. 2 illustrates, the degree of expansion or compression in any given element is indicated not by its velocity magnitude (speed) value alone, but rather by the change in magnitude of the velocity between the element and its surrounding region of elements. There could, for example, be very fast flow of blood through an artery, with little expansion of the surrounding arterial tissue and no expansion of the blood itself (which is an incompressible fluid). As another example, a relatively hard lump in otherwise homogeneous tissue would normally exhibit less elasticity and compression than its surrounding tissue.

In FIG. 2, notice also that the direction of movement changes relatively quickly from column j=10 to columns j=11, 12; the speed of movement is roughly the same, but the direction of the arrows is "rotating" counterclockwise (about the +z-axis). This may indicate a boundary region (j=11,12) between two tissue layers (j=10 and j=13), or that the two tissue layers are torn or otherwise separated, thus causing non-uniform motion between them. In this case, notice that the quantity of interest once again is not just the speed (magnitude of velocity) but rather the degree of change of direction of the velocity. As another example, in the context of fluid flow, quickly changing velocity directions might indicate turbulence, which might occur near arterial obstructions or areas of heart valve damage (creating heart "murmurs").

Recall now the following concepts and notation from the field of vector analysis:

$$\nabla = \left( \frac{\partial}{\partial x}, \frac{\partial}{\partial y}, \frac{\partial}{\partial z} \right)$$

As is well known, the vector "$\nabla$" indicates the operation of partial differentiation in the three orthogonal directions x, y and z. (For analyzing motion in a plane, for example the x-y plane, $\nabla$ reduces to a two-element vector, without the z-direction differentiation.)

Now let $\bar{v}_{i,j} = (v_x, v_y, v_z)$, where $v_x, v_y,$ and $v_z$ are the x-y-z components of $\bar{v}_{i,j}$. The divergence of $\bar{v}_{i,j}$ is defined as:

$$div\bar{v} = \nabla \cdot \bar{v} = \frac{\partial v_x}{\partial x} + \frac{\partial v_y}{\partial y} + \frac{\partial v_z}{\partial z}$$

where "·" indicates the well-known dot or inner vector product. This scalar quantity is known from the theory of vector analysis, and is a measure of the degree of volumetric increase or decrease of $\bar{v}$ at the point where the divergence is calculated.

The rotation or "curl" of $\bar{v}$ is defined as:

$$rot\bar{v} = \nabla \times \bar{v} = \begin{vmatrix} \bar{e}_x & \bar{e}_y & \bar{e}_z \\ \frac{\partial}{\partial x} & \frac{\partial}{\partial y} & \frac{\partial}{\partial z} \\ v_x & v_y & v_z \end{vmatrix} =$$

$$\left( \frac{\partial v_z}{\partial y} - \frac{\partial v_y}{\partial z}, \frac{\partial v_x}{\partial z} - \frac{\partial v_z}{\partial x}, \frac{\partial v_y}{\partial x} - \frac{\partial v_x}{\partial y} \right)$$

where: "x" indicates the well-known cross or outer vector product; and $\bar{e}_x, \bar{e}_y,$ and $\bar{e}_z$ are the unit vectors in the x, y and z directions, respectively. The vector $\nabla \times \bar{v}$ is also known from the theory of vector analysis, and is a measure of the amount of rotation about the three axes of the vector $\bar{v}$ at the point of calculation.

According to one embodiment of the invention, the processing system 102 computes the divergence of the velocity for each image element (or predetermined groupings of elements) at positions (i,j). According to another embodiment of the invention, the processing system 102 computes the rotation of the velocity for each image element (or predetermined groupings of elements) at positions (i,j). After conventional scaling as needed, the processing system then passes on the velocity divergence or rotation values to the display driver 130 for display on the screen 132.

It is not necessary to include both a divergence-processing mode and a rotation-processing mode in the same system. If both are included, however, the processing system 102 will sense the appropriate input from the user to determine in which mode it should operate. Note that it is possible for the system to switch quickly between modes, since the same velocity field information $\bar{v}_{i,j}$ (stored in memory portion 121) is used as the basis for calculations in both display modes.

The divergence values are scalars, regardless of whether the imaging is 2-D or 3-D. These values can therefore be displayed as if they were conventional brightness values (the greater the divergence, the brighter the pixel, for example) or colors (increasing redness with increasing divergence, for example), or both.

At each point, the rotation of the velocity vector will also be a vector, with as many components as the velocity vectors themselves. One way to display the rotation for each point is to calculate and display its magnitude by varying pixel brightness, that is, $|\nabla \times \bar{v}_{i,j}|$ is displayed for the pixel at position (i,j) such that the brightness of the pixel is proportional or otherwise related to the magnitude. Color-coding may also be used.

Displaying the magnitude of the rotation at each point would give information only about the degree to which any rotation at all is taking place at the point in question. This may, however, be sufficient in many applications. For example, directional information may be unnecessary for interpretation and identification of a problem such as an arterial obstruction or a tear between two different tissue layers. The very fact that the flow is not substantially laminar may indicate a problem.

Alternatively, the processing system could calculate and display a projection of the rotation vector either onto a 2-D plane (for example, the scan plane), or in a single chosen direction (for example, a line parallel to the transducer array in the scan plane). If directional information is important, the system could, as one example, average the vectors over predetermined pixel groups and generate and display small arrows similar to those shown in FIG. 2, but representing the projected rotations. Streamlines could also be superimposed over the display of rotational magnitude. Color-coding analogous to current velocity displays may also be used.

In order to allow for proper display formatting, the divergence and/or rotation values for at least a current frame are preferably stored in a divergence memory portion 140 and a rotation memory portion 142, respectively, of the memory 118. This memory storage may also include recording the values (formatted for display or not) on a permanent storage medium such as a cine memory.

Many applications of the invention will not be able to measure velocity components in three dimensions, but rather will generate only 2-D frame data. In these cases, the appropriate directional component of the divergence calculation is omitted. This omission will in most cases still provide valuable information—most 2-D cross-sections of expanding or contracting 3-D regions will themselves still exhibit regions of expansion and contraction. For examining fluid/tissue boundaries, such as arterial expansion and contraction, the general direction(s) of flow will in most cases be known and the operator can then select the scan plane (by moving the transducer) that shows the most significant divergence display. The user can also instruct the system (for example, by activating a switch or knob or by entering appropriate, conventional commands into the input unit) to switch between conventional brightness- or Doppler-mode imaging and the divergence- or rotation-imaging modes according to the invention. The operator could thereby first get a general idea of the geometry of the interrogation region and would then know how best to position the transducer for the best divergence or rotation display. The operator will be able to determine such scan planes with practice and conventional training.

In order to derive divergence or rotational information from the velocity vector field, there must be some movement within the scanned interrogation region. This will occur naturally in some applications, such as where the system is used to generate and display velocity field information for a fluid such as blood is flowing in an artery or an organ such as the heart. Natural changes in blood pressure may also induce movement into surrounding tissue, which the system according to the invention may then sense and analyze. In other cases, the operator may need to induce motion, and thus expansion, compression and possibly rotation of the underlying tissue. The operator can do this in different ways. For example, the operator may apply the time-honored methods of manual palpation (mentioned above) of a patient, or he may press and move the transducer against the patient's skin, or both. The physician operator can then watch the display screen and follow how the tissue responds with respect to velocity divergence and/or rotation.

The velocity data generated for an image frame using conventional ultrasonic transducers and systems tends to be noisy. As such, any differentiation of such data could be greatly affected by the noise and thus greatly reduce the reliability and usefulness of any calculations based on derivatives. Calculation of both the divergence and the rotation of the velocity vector field, however, requires the calculation of partial derivatives.

Consequently, according to the invention, the velocity data $\bar{v}_{i,j}$ is preferably smoothed before, after, or, indeed, at the same time as, the system calculates divergence and/or rotation. (Smoothing may be omitted if it is known that the velocity data has, or is otherwise pre-filtered to have, less than some experimentally determined, acceptable noise level.) Any conventional smoothing procedures may be used and can be found in most modern texts on digital signal processing. Smoothing may be either temporal or spatial, and either or both may be used in the invention.

For temporal smoothing, the velocity value at each given tissue position is averaged over time, for example, over a pre-determined previous number n of image frames. Thus, $\bar{v}_{i,j}^*$, the velocity value used for the image frame at time t, is set equal to:

$$w_0 \cdot \bar{v}_{i,j}(t) + w_1 \cdot \bar{v}_{i,j}(t-1) + \ldots + w_n \cdot \bar{v}_{i,j}(t-n)$$

where $w_0, w_1, \ldots, w_n$ are weighting coefficients, which may be determined (or omitted altogether) using normal theoretical and experimental methods; and (t–p) is the image frame generated p time units earlier.

In order to ensure that the velocity values are from the same pixel (remember, the tissue is supposedly moving, and the transducer may itself be moving), any conventional registration technique may be used. Indeed, the previously generated velocity values—possibly weighted—may be used to perform or aid in frame registration, since they indicate in which direction and how fast the tissue is moving from one frame to the next.

As one example of spatial smoothing, each current velocity value is set equal to a weighted (as needed) average of the velocity values in a predetermined pixel region that surrounds the current pixel and that has the current value at its center. Other methods are known and may be used. The type(s) of smoothing used (if any) may be determined using conventional experimentation and calculations. Note that the invention provides for real-time calculation of the divergence or rotation of the velocity vector field.

Central to the calculations of both velocity divergence ($\nabla \cdot \bar{v}$) and rotation or curl ($\nabla \times \bar{v}$) is the calculation of the first partial derivatives of the velocity vectors, that is, of $\partial \bar{v}/\partial x$, $\partial \bar{v}/\partial y$, and $\partial \bar{v}/\partial z$, (spatial velocity changes) after any smoothing. Most modern texts on numerical analysis discuss methods for estimating the derivative(s) of a discretized functions such as the velocity field generated by the invention. Any of these methods may be used according to the invention; the best method can be determined using conventional calculations and experimentation. In general, these methods rely on forming a weighted difference between the value at the current pixel (or other image element) position and the values for a predetermined number of the pixels on one or both sides of the current pixel in the direction of the variable of differentiation.

Refer to FIG. 2. As the simplest example of estimating $\partial \bar{v}/\partial y$ at the point (i,j)=(5,6), the system could calculate $(v_y(6,6)-v_y(5,6))/\delta$, where $\delta$ is a normalization function or constant equal or at least corresponding to (with scaling) the distance in the y-direction between the centers of the two pixels. The normalization function or constant may be applied at any point in the calculations of velocity, or of divergence or rotation.

Other known methods using more neighboring velocity values, on either side of the pixel of interest, may be used and will in general be more robust, that is, less sensitive to local noise. Partial derivatives in other directions may be calculated in an analogous manner. Note that, depending on the methods used, the steps of spatial smoothing and differentiation may in many cases be performed at the same time by combining the respective routines into one.

The invention determines changes in properties of the field of velocity vectors (in particular, the divergence and rotation) for a scanned image region. Such properties will normally also be pronounced at the boundaries between two types of tissue, for example, between layers of tissue with different elasticity, or between regions of fluid and non-fluid, for example, between blood and the wall of a blood vessel. As such, the invention can be used to detect such edges and boundaries.

In some applications, one wishes not only to detect but also to enhance the image of an edge, such as when trying to image the boundary between two layers of tissue. If the two layers have similar acoustic properties, but different elasticities, then the invention may be able to detect an edge (especially in the divergence display mode) better than a conventional B-mode scan would.

In other applications, one wishes to identify boundaries in order to eliminate their effects on other calculations. For example, in Doppler imaging, one may wish to filter out the echo from the wall of the vessel in which blood flows. The invention may in such applications be used to identify just where the wall is, and thus to better isolate and filter out the signal echoed from it.

I claim:

1. A method for generating and displaying an image of an interrogation region of a patient's body comprising the following steps:

scanning the interrogation region with an ultrasonic probe;

sensing ultrasonic return signals returned from a scattering medium in the interrogation region;

generating at least one input data frame representing the scanned interrogation region as a pattern of velocity values, each velocity value corresponding to the velocity of the scattering medium in a respective portion of the interrogation region;

calculating and generating a pattern of spatial velocity change values as a predetermined function of local, spatial differential changes of the respective velocity values; and displaying the scanned interrogation region as the pattern of spatial velocity change values.

2. A method as defined in claim 1, in which each spatial velocity change value is a predetermined function of the divergence ($\nabla \cdot$) of a corresponding one of the velocity values.

3. A method as defined in claim 1, in which each spatial velocity change value is a predetermined function of the rotation ($\nabla \times$) of a corresponding one of the velocity values.

4. A method as defined in claim 1, in which the step of generating the pattern of spatial velocity change values as a predetermined function of the velocity values includes smoothing the velocity values.

5. A system for generating and displaying an image of an interrogation region of a patient's body comprising:

ultrasonic probe means for scanning the interrogation region and for sensing ultrasonic return signals returned from a scattering medium in the interrogation region;

processing means for generating at least one input data frame representing the scanned interrogation region as a pattern of velocity values, each velocity value corresponding to the velocity of the scattering medium in a respective portion of the interrogation region and for calculating and generating a pattern of spatial velocity change values as a predetermined function of local, spatial differential changes of the respective velocity values; and display means for displaying the scanned interrogation region as the pattern of spatial velocity change values.

6. A system as defined in claim 5, in which the processing means is further provided for generating each spatial velocity change value as the divergence ($\nabla \cdot$) of the corresponding one of the velocity values.

7. A system as defined in claim 5, in which the processing means is further provided for generating each spatial velocity change value as the rotation ($\nabla \times$) of the corresponding one of the velocity values.

8. A system as defined in claim 5, in which the processing means is further provided for smoothing the velocity values.

9. A method for generating and displaying an image of an interrogation region of a patient's body comprising the following steps:

scanning the interrogation region with an ultrasonic probe;

sensing ultrasonic return signals returned from a scattering medium in the interrogation region;

generating at least one input data frame representing the scanned interrogation region as a pattern of velocity values, each velocity value corresponding to the velocity of the scattering medium in a respective portion of the interrogation region;

calculating and generating a pattern of spatial velocity change values, each spatial velocity change value being calculated as a predetermined function of the divergence ($\nabla \cdot$) of a corresponding one of the velocity values; and displaying the scanned interrogation region as the pattern of spatial velocity change values.

10. A method for generating and displaying an image of an interrogation region of a patient's body comprising the following steps:

scanning the interrogation region with an ultrasonic probe;

sensing ultrasonic return signals returned from a scattering medium in the interrogation region;

generating at least one input data frame representing the scanned interrogation region as a pattern of velocity values, each velocity value corresponding to the velocity of the scattering medium in a respective portion of the interrogation region;

calculating and generating a pattern of spatial velocity change values, each spatial velocity change value being calculated as a predetermined function of the rotation ($\nabla \times$) of a corresponding one of the velocity values; and displaying the scanned interrogation region as the pattern of spatial velocity change values.

11. A system for generating and displaying an image of an interrogation region of a patient's body comprising:

ultrasonic probe means for scanning the interrogation region and for sensing ultrasonic return signals returned from a scattering medium in the interrogation region;

processing means
for generating at least one input data frame representing the scanned interrogation region as a pattern of velocity values, each velocity value corresponding to the velocity of the scattering medium in a respective portion of the interrogation region; and
for calculating and generating a pattern of spatial velocity change values, each spatial velocity change value being calculated as a predetermined function of the divergence ($\nabla \cdot$) of a corresponding one of the velocity values; and display means for displaying the scanned interrogation region as the pattern of spatial velocity change values.

12. A system for generating and displaying an image of an interrogation region of a patient's body comprising:

ultrasonic probe means for scanning the interrogation region and for sensing ultrasonic return signals returned from a scattering medium in the interrogation region;

processing means for generating at least one input data frame representing the scanned interrogation region as a pattern of velocity values, each velocity value corresponding to the velocity of the scattering medium in a respective portion of the interrogation region; and for calculating and generating a pattern of spatial velocity change values, each spatial velocity change value being calculated as a predetermined function of the rotation ($\nabla \times$) of a corresponding one of the velocity values; and display means for displaying the scanned interrogation region as the pattern of spatial velocity change values.

* * * * *